하지 않음

United States Patent [19]

Vorpahl

[11] Patent Number: 5,770,388
[45] Date of Patent: *Jun. 23, 1998

[54] METHOD OF SEPARATION EMPLOYING MAGNETIC PARTICLES AND SECOND MEDIUM

[75] Inventor: John Vorpahl, Livermore, Calif.

[73] Assignee: Dade Behring Marburg GmbH, Deerfield, Ill.

[*] Notice: The portion of the term of this patent subsequent to Jan. 18, 2011, has been disclaimed.

[21] Appl. No.: 168,263

[22] Filed: Dec. 13, 1993

Related U.S. Application Data

[63] Continuation of Ser. No. 455,550, Dec. 22, 1989, Pat. No. 5,279,936.

[51] Int. Cl.$^6$ .................................................. G01N 33/53
[52] U.S. Cl. .......................... 435/7.25; 435/7.2; 435/7.21; 435/7.9; 435/7.92; 435/7.94; 436/501; 436/518; 436/514; 436/526; 436/806; 436/824
[58] Field of Search ................. 435/6, 5, 7.9, 7.92–7.95, 435/7.25, 2, 7.1, 7.2, 7.21; 436/501, 512, 513, 518, 526, 536, 538, 525, 529, 533, 514, 806, 824

[56] References Cited

U.S. PATENT DOCUMENTS

| | | |
|---|---|---|
| 3,933,997 | 1/1976 | Hersh et al. . |
| 3,970,518 | 7/1976 | Giaever .............................. 436/526 X |
| 4,018,886 | 4/1977 | Glaever . |
| 4,070,246 | 1/1978 | Kennedy et al. . |
| 4,115,534 | 9/1978 | Ithakissios . |
| 4,115,535 | 9/1978 | Glaever . |
| 4,285,819 | 8/1981 | Yen et al. . |
| 4,413,070 | 11/1983 | Rembaum . |
| 4,452,773 | 6/1984 | Molday . |
| 4,454,234 | 6/1984 | Czerlinski . |
| 4,523,996 | 6/1985 | Charles et al. . |
| 4,526,681 | 7/1985 | Friedlaender et al. . |
| 4,731,337 | 3/1988 | Luotola et al. ......................... 436/526 |
| 4,777,145 | 10/1988 | Luotola et al. . |
| 4,783,401 | 11/1988 | Horan et al. ............................... 435/34 |
| 4,868,130 | 9/1989 | Hargreaves ............................. 436/526 |
| 4,935,147 | 6/1990 | Ullman et al. .......................... 210/695 |
| 5,073,341 | 12/1991 | Hargreaves ............................... 422/58 |
| 5,279,936 | 1/1994 | Vorpahl ....................................... 435/6 |

FOREIGN PATENT DOCUMENTS

| | | |
|---|---|---|
| 2 019 378 | 10/1979 | United Kingdom . |
| 2 152 664 | 8/1985 | United Kingdom . |
| 864684 | 8/1986 | WIPO . |
| WO 86 04684 A1 | 8/1986 | WIPO . |

OTHER PUBLICATIONS

Weaver, et al., "Gel Microdroplets: Rapid Detection and Enumeration of Individual Microorganisms by Their Metabolic Activity", *Biotechnology*, (1988) vol. 6, pp. 1084–1089.

Henning et al., "Isolation of Rat Liver Lysosomes by Loading with Colloidal Gold", *Biochim. Biophys. Acta* (1974) vol. 354, pp. 114–120.

Dorn et al., "Blood Culture Technique Based on Centrifugation: Developmental Phase", *J. Clin. Micro.* (1976) vol. 3, pp. 251–257.

Leduc et al., "Visualization of Poly (ADP–ribose) Synthetase Associated with Polynucleosomes by Immunoelectron Microscopy", *Biochim. Biophys. Acta* (1986) vol. 885, pp. 248–255.

Courtoy, et al., "Shift of Equilibrium Density Induced by 3,3'–Diaminobenzidine Cytochemistry: A New Procedure for the Analysis and Purification of Peroxidase–containing Organelles", *J. Cell Biology* (1984) vol. 98, pp. 870–876.

Dutton et al., "Iron–Dextran Antibody Conjugates: General Method for Simultaneous Staining of Two Components in High–Resolution Immunoelectron Microscopy", *Proc. Natl. Acad. Sci.* (1979) vol. 76, pp. 3392–3396.

Ithakissios, et al., "Use of Protein Containing Magnetic Microparticles in Radioassays", *Clin. Chem.* (1977) vol. 23, pp. 2072–2079.

Molday, et al., "Separation of Cells Labeled with Immunospecific from Dextran Microspheres Using High Gradient Magnetic Chromatography" *FEBS* (1984) vol. 170, pp. 232–238.

Molday, et al., "Immunospecific Ferromagnetic Iron–Dextran Reagents for the Labeling and Magnetic Separation of Cells", *J. Immunol. Meth.* (1982) vol. 52, pp. 353–357.

Molday, et al., "Application of Magnetic Microspheres in Labelling and Separation of Cells", *Nature* (1977) vol. 268, pp. 437–438.

Nargessi, et al., "Solid–Phase Fluoroimmunoassay of Human Albumin in Biological Fluids", *Clin. Chim. Acta* (1978) vol. 89, pp. 455–460.

Nye, et al., "Solid–Phase, Magnetic Particle Radioimmunoassay", *Clin. Chim. Acta* (1976) vol. 69, pp. 387–396.

Rosenweig, "Magnetic Fluids", *Scien. Amer.* (1983) vol. 10, pp. 136–145.

(List continued on next page.)

*Primary Examiner*—Susan Wolski
*Attorney, Agent, or Firm*—Leland K Jordan; Jerome Rosenstock; Theodore J. Leitereg

[57] ABSTRACT

Methods are disclosed for separating a component of interest from a mixture containing the component of interest and other components. The method comprises contacting a first liquid medium containing the component of interest and other components with a second liquid medium that is of different density than and/or of different viscosity than the first liquid medium. The contact is carried out in such a way that mixing of the media is minimized or avoided. The component of interest is bound to magnetic particles. The contacted first liquid medium and second liquid medium are subjected to a magnetic field gradient to allow the magnetic particles to migrate into the second liquid medium and separation of the component of interest from other components is realized. Also disclosed are assays employing the present method. Kits for carrying out the present method and assays are also disclosed.

19 Claims, No Drawings

OTHER PUBLICATIONS

Widder, et al., "Magnetic Protein A Microspheres: A Rapid Method for Cell Separation", *Clin. Immunol. and Immunopath.* (1979) vol. 14, pp. 395–400.

Baldwin, et al., "Biomat: A Rapid, Self–Washing Immunoassay System with a Microparticulate Solid Phase", *Clinical Chemistry* (1987) vol. 33:9, pp. 1566–1567.

Freifelder, D., *Molecular Biology* (1983) Science Book Int'l Publishers, pp. 88–91.

Owen Beckman, Mitch Griffith, *Techniques Preparative, Zonal, and Continuous Flow Ultracentrifugation,* pp. 3, 10, 11.

Harlow et al., "Antibodies: A Laboratory Manual", Cold Spring Laboratory, (1988), pp. 547–549.

METHOD OF SEPARATION EMPLOYING MAGNETIC PARTICLES AND SECOND MEDIUM

This is a continuation of application Ser. No. 07/455,550, filed Dec. 22, 1989, now U.S. Pat. No. 5,279,930.

BACKGROUND OF THE INVENTION

This invention relates to methods for separating a component which may or may not be particulate, from other components in a liquid medium using magnetic particles and a second liquid medium. The invention has particular application to separation of cells from biological fluids such as blood, lymphatic fluid, urine, cell cultures, etc., microorganisms, organelles, molecular aggregates, nucleic acids, and ligands.

Detection and identification of microorganisms, particularly in biological samples and food and drug products, are required for clinical diagnosis of disease, prevention of disease transmission, and food quality. Traditionally, bacteria and fungi are detected and identified by culture methods, which are notoriously slow and tedius. More recently, immunoassays for microbial antigens and nucleic acid probe assays have been developed. However, these methods usually only permit detection of a specific organism. In determination of septicemia, as assay for a general indicator of growth, such as carbon dioxide, is often used. This is followed by culture methods to identify the organism and then by antibiotic susceptibility testing. There is a need to obtain test results more rapidly with less labor.

Several techniques are known for carrying out separations. For example, in ligand binding assays one may employ centrifugation and washing; differential migration of bound and free fractions, e.g., chromatoelectrophereses, gel filtration, etc.; chemical precipitation of the bound or free fraction, e.g., by means of organic solvents, salts, acids, etc. followed by filtration or centrifugation; immunological precipitation of the bound fraction, e.g., by double antibody technique followed by filtration or centrifugation; absorption of the bound or free fraction onto selective sorbing media, e.g., charcoal, silicates, resins, etc.; magnetic separation techniques, and the like.

Magnetic separations generally fall into two general categories. There are those separations in which the material to be separated is intrinsically magnetic. On the other hand, one or more components of a mixture can be rendered magnetic by the attachment of a magnetically responsive entity. In biochemical separations, materials of interest are generally not sufficiently magnetic and thus magnetic particles bound to antibodies, lectins, and other targeting molecules have been used for isolating many of these materials. Magnetic particles targeted for specific molecules have also been used in a variety of immunoassays.

Many of the separation techniques, including those used in immunoassays, are relatively long and complicated procedures. Such procedures reduce operator efficiency, decrease thoughput, and increase the costs of tests. Other separation techniques which are rapid and simple do not adequately distinguish between the bound and free fractions and therefore are unsuited for immunoassays or can only be utilized in a limited number of tests.

In a particular application of separation techniques, red cell washing to remove unbound IgG is one of the most critical steps of the antibody screen, which is designed to detect relatively uncommon antibodies in blood that bind to heterologous erythrocyte antigens. Due to the relatively high level of IgG in normal human plasma (about 10 mg/ml), exhaustive washing of the erythrocytes is required prior to detection of antibodies bound to the erythrocytes. A typical manual assay uses 3 or 4 wash cycles with 3–5 mls of saline per cycle. Inefficient cell washing can cause partial or complete neutralization of Coombs reagent (anti-human IgG) that is used for detection of bound antibodies by causing red cell agglutination when antibodies are present.

DESCRIPTION OF THE RELATED ART

U.S. application Ser. No. 262,771 filed Oct. 26, 1988 (continuation of U.S. application Ser. No. 811,202 filed Dec. 20, 1985) describes a method for separating a substance from a liquid medium. The method comprises combining the liquid medium containing the substance with magnetic particles under conditions for non-specific chemical binding of the magnetic particles. Thereafter, the medium is subjected to a magnetic field gradient to separate the particles from the medium. The preferred non-specific binding is achieved as the result of charge interactions between the particles usually by means of a polyionic reagent. The above method has particular application to the separation of cells and microorganisms from aqueous suspensions and also to the determination of an analyte in a sample suspected of containing the analyte.

Recently, Microdrop Co. published a method for converting an entire sample of urine into small beads of agarose or other gel such that each bead traps at most one organism (Weaver, et al., *Biotechnology* (1988) 6:1084–1089). The beads included a culture medium and were dispersed in oil. Growth was directly detected by the formation of an indicator dye in the infected particles. The method offers the ability to detect, sort, count, and study individual organisms. However the method is cumbersome and fails to separate the bacteria from growth inhibiting substances in the sample.

Cells are commonly separated by centrifugation in high density or high viscosity media, and lysosomes that have incorporated gold particles have been isolated by virtue of their increased density using sucrose density gradient velocity centrifugation (Henning, et al, *Biochim. Biophys. Acta.* 354 (1974) 114–120. Also, Dorn et al., *J. Clin. Micro* 3 (1976) 251–257 demonstrated that bacteria along with insoluble cellular debris can be separated from the soluble components of a lysed blood sample by spinning the suspension with an underlying layer of sucrose solution. This is the basis of a product from I.E. DuPont de Nemours Company called the ISOLATOR. Further, Leduc et al. (*Biochim. Biophys. Acta.* 885 (1986) 248) separated polynucleosomes bearing poly-ADP-ribose synthetase on their surface from unbound polynucleosomes by causing specific antibodies to the synthetase to bind, combining the mixture with gold-labeled protein A and separating by sucrose gradient velocity sedimentation whereupon the gold bond polynucleosomes separated more rapidly. Courtoy, et al. (*J. Cell Biology,* 98 (1984) 870–876) have described the shift of equilibrium density induced by 3,3'-diaminobenzidine cytochemistry in a procedure for the analysis and purification of peroxidase containing organelles.

A method for determining the concentration of substances in biological fluids (e.g., drugs, hormones, vitamins and enzymes) wherein magnetically responsive, permeable, solid, water insoluble, microparticles are employed is disclosed in U.S. Pat. No. 4,115,534. Functional magnetic particles formed by dissolving a mucopolysaccharide such as chitosan in acidified aqueous solution containing a mixture of ferrous chloride and ferric chloride is disclosed in U.S.

Pat. No. 4,285,819. The microspheres may be employed to remove dissolved ions from waste aqueous streams by formation of chelates. U.S. Pat. No. 3,933,997 describes a solid phase radioimmunoassay for digoxin where anti-digoxin antibodies are coupled to magnetically responsive particles. Small magnetic particles coated with an antibody layer are used in U.S. Pat. No. 3,970,518 to provide large and widely distributed surface area for sorting out and separating select organisms and cells from populations thereof. U.S. Pat. No. 4,018,886 discloses small magnetic particles used to provide large and widely distributed surface area for separating a select protein from a solution to enable detection thereof. The particles are coated with a protein that will interact specifically with the select protein. U.S. Pat. No. 4,070,246 describes compositions comprising stable, water insoluble coatings on substrates to which biologically active proteins can be covalently coupled so that the resulting product has the biological properties of the protein and the mechanical properties of the substrate, for example, magnetic properties of a metal support.

A diagnostic method employing a mixture of normally separable protein-coated particles is discussed in U.S. Pat. No. 4,115,535. Microspheres of acrolein homopolymers and copolymer with hydrophilic comonomers such as methacrylic acid and/or hydroxyethylmethacrylate are discussed in U.S. Pat. No. 4,413,070. U.S. Pat. No. 4,452,773 discloses magnetic iron-dextran microspheres which can be covalently bonded to antibodies, enzymes and other biological molecules and used to label and separate cells and other biological particles and molecules by means of a magnetic field. Coated magnetizeable microparticles, reversible suspensions thereof, and processes relating thereto are disclosed in U.S. Pat. No. 4,454,234. A method of separating cationic from anionic beads in mixed resin beds employing a ferromagnetic material intricately incorporated with each of the ionic beads is described in U.S. Pat. No. 4,523,996. A magnetic separation method utilizing a colloid of magnetic particles is discussed in U.S. Pat. No. 4,526,681. UK Patent Application GB 2,152,664A discloses magnetic assay reagents.

UK Patent GB 2,019,378 describes a process for the flocculation of organic or inorganic matter utilizing magnetic particles.

An electron-dense antibody conjugate made by the covalent bonding of an iron-dextran particle to an antibody molecule is reported by Dutton, et al. (1979) *Proc. Natl. Acad. Sci.* 76:3392–3396. Ithakissios, et al. describes the use of protein containing magnetic microparticles in radioassays in *Clin. Chem.* 23:2072–2079 (1977). The separation of cells labeled with immunospecific iron dextran microspheres using high gradient magnetic chromatography is disclosed by Molday, et al. (1984) *FEBS* 170:232–238. In *J. Immunol. Meth.* 52:353–367 (1982) Molday, et al. describe an immuno specific ferromagnetic iron-dextran reagent for the labeling and magnetic separation of cells. An application of magnetic microspheres in labeling and separation of cells is also disclosed by Molday, et al. in *Nature* 268:437–438 (1977). A solid phase fluoroimmunoassay of human albumin and biological fluids is discussed by Nargessi, et al. (1978) *Clin. Chim. Acta.* 89:455–460. Nye, et al. (1976) *Clin. Chim. Acta.* 69:387–396 discloses a solid phase magnetic particle radioimmunoassay. Magnetic fluids are described by Rosenweig (1983) *Scien. Amer.* 10:136–194. Magnetic protein A microspheres and their use in a method for cell separation are disclosed by Widder, et al. (1979) *Clin. Immunol. and Immunopath.* 14:395–400.

SUMMARY OF THE INVENTION

The method of the present invention is directed to the separation of a component of interest from other components in a mixture by causing the binding of the component of interest to magnetic particles. Where the component of interest is present as a non-particulate solute, it will normally bind to the magnetic particles through specific ligand-receptor binding or non-specific binding such as through electrostatic or hydrophobic interactions. A first liquid medium containing the component of interest bound to magnetic particules and the other components of the mixture is contacted with, without mixing with, a second liquid medium that is of different density than and/or of different viscosity than the first medium. Next, the media are subjected to a magnetic field gradient to cause the magnetic particles to migrate from the first liquid medium into the second liquid medium.

The method of the present invention has particular application to the separation of organic and biochemical components of interest from, for example, cell cultures, body fluids and the like.

One embodiment of a method in accordance with the present invention is a method for separating cells from a mixture containing the cells and other components. The method comprises layering a first liquid medium containing the cells and other components with a second medium that is of different density than and/or of different viscosity than the first liquid medium. The cells are bound to superparamagnetic or paramagnetic particles (cell-particles). The layered first liquid medium and the second liquid medium are subjected to a magnetic field gradient sufficient to cause the cell-particles to migrate into the second liquid medium. In a further embodiment of the above method the cell-particles are separated from the second liquid medium. In a further embodiment of the above method the binding of the cells and the magnetic particles is reversed.

Another embodiment of the present invention involves a method for separating erythrocytes from immunoglobulins in a blood sample. The method comprises combining the blood sample with magnetic particles of 10 to 100 nm average diameter and a cationic polymer in a buffered aqueous medium. The aqueous medium is layered with a second aqueous solution having a viscosity greater than the aqueous medium. The layered media are subjected to a magnetic field gradient to cause the cells and magnetic particles to migrate into the second aqueous solution. Next, the cells are separated from the second aqueous solution.

Another aspect of the invention is a method for conducting an assay for an analyte. The assay comprises contacting a first liquid medium containing the analyte, or a substance whose presence is related to the presence of the analyte, with a second liquid medium that is of different density and/or viscosity than the first liquid medium without mixing the media. The analyte or the substance is bound to magnetic particles. The media are then subjected to a magnetic field gradient to allow the magnetic particles to migrate into the second liquid medium. The analyte or the substance is then detected.

The invention further includes kits for conducting the methods and assays of the invention.

DESCRIPTION OF THE SPECIFIC EMBODIMENTS

The present invention relates generally to a method of separating a component of interest (CI) from other components in a sample. The CI to be separated will be bound to, or will be caused to bind to, magnetic particles. The preferred approaches for achieving binding between the magnetic particles and the CI are charge interactions and ligand-receptor binding. CI bound to magnetic particles (CIMP) are separated from a first liquid medium containing the CIMP by the use of a second liquid medium and a magnetic field gradient. The separated CIMP can be washed further and examined by physical or chemical methods. The CIMP can also be treated to reverse the binding with CI. Reversal of binding can be followed by separation of the free magnetic particles to provide a means of separating the CI from the magnetic particles.

The present method has wide application in the field of the separation of a component of interest from other components in a sample particularly for separating biological materials, such as particulate material, e.g., cells, microorganisms, organelles, molecular aggregates, and the like and non-particulates, e.g., ligands and nucleic acids. The invention provides a separation method which is more convenient and complete than centrifugation, filtration, and prior magnetic separation methods and is particularly applicable to the pretreatment of suspensions where it is desired to carry out an analysis of the component of interest separated from other components. The invention has application to the assay of an analyte in a sample where a separation step is required. The separation method of the invention is exceptionally efficient because the component of interest is washed by the second medium during separation.

Before proceeding further with the description of the specific embodiments of the present invention, a number of terms will be defined.

Component of interest (CI)—the compound or composition to be separated. The component of interest can be non-particulate or particulate. Non-particulate CI can be comprised of a member of a specific binding pair (sbp) and may be a ligand, which is mono- or polyvalent, usually antigenic or haptenic, and is a single compound or plurality of compounds which share at least one common epitopic or determinant site. The CI can also be a particle. Exemplary of a CI that is a particle are cells such as bacteria or a cell bearing a blood group antigen such as A, B, D, etc., or an HLA antigen or a microorganism, e.g., bacterium, fungus, protozoan, or virus.

The CI can be an analyte, either monovalent (monoepitopic) or polyvalent (polyepitopic). The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes include drugs, metabolites, pesticides,. pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc. Illustrative microorganisms include:

| | |
|---|---|
| Corynebacteria | |
| *Corynebacterium diphtheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. ducryi* | *Rhizopus arrhizua* Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | Fonsecaea compact |
| Pasteurellae | *Fonsecaea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |

-continued

| | |
|---|---|
| *Clostridium bifermentans* | Virus B |
| *Clostridium sporogenes* | Cytomegalovirus |
| Mycobacteria | Pox Viruses |
| | |
| *Mycobacterium tuberculosis hominis* | Variola (smallpox) |
| *Mycobacterium bovis* | Vaccinia |
| *Mycobacterium avium* | Poxvirus bovis |
| *Mycobacterium leprae* | Paravaccinia |
| *Mycobacterium paratuberculosis* | *Molluscum contagiosum* |
| Actinomycetes (fungus-like bacteria) | Picornaviruses |
| | |
| Actinomyces Isaeli | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| | |
| The Spirochetes | Influenza(A, B, and C) |
| | |
| *Treponema pallidum*    *Spirillum minus* | Parainfluenza (1–4) |
| *Treponema pertenue*    *Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| | |
| Mycoplasmas | Arboviruses |
| | |
| *Mycoplasma pneumoniae* | |
| Other pathogens | Eastern Equine Eucephalitis Virus |
| | |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| | |
| *Rickettsia prowazekii* | California Encephalltis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| | |
| *Rickettsia sibiricus* | Reovirus Types 1–3 |
| | Retroviruses |
| | |
| *Rickettsia akari* | Human Immunodeficiency Viruses (HIV) |
| *Rickettsia tsutsugamushi* | Human T-cell Lymphotrophic |
| | Virus I & II (HTLV) |
| *Rickettsia burnetti* | Hepatitis |
| | |
| *Rickettsia quintana* | Hepatitis A Virus |
| Chlamydia (unclassifiable parasites bacterial/viral) | Hepatitis B Virus |
| | Hepatitis nonA-nonB Virus |
| | |
| Chlamydia agents (naming uncertain) | Tumor Viruses |
| | |
| Fungi | Rauscher Leukeuia Virus |
| | |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidloides brasiliensis* | |
| *Candida albicans* | |
| *Aspergillus fumigatus* | |
| *Mucor corymbifer (Absidia corymbifera)* | |

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand-any organic compound for which a receptor naturally exists or can be prepared.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Particulate CI—the particulate CI are non-magnetic, i.e., diamagnetic or paramagnetic usually with a magnetic susceptibility (x) of less than $1 \times 10^{-5}$ emu/Oecm$^3$. The particulate CI are generally at least about 0.1 microns and not more than about 100 microns in diameter usually 0.5 to 25 microns. The particulate CI may be organic or inorganic, swellable or non-swellable, porous or non-porous, usually of a density approximating water, generally from about 0.7 to about 1.5 g/ml. Usually the particulate CI will have a charge, either positive or negative, and may have sbp members on their surface. Normally, the particulate CI will be biologic materials such as cells such as e.g., erythrocytes, leukocytes, lymphocytes, hybridomas, microorganisms such as, e.g., streptococcus, staphylococcus aureus, E. coli, viruses; organelles, such as, nuclei, mitochondria, nucleosomes, and the like. The particulate CI can also be particles comprised of organic and inorganic polymers, liposomes, latex particles, phospholipid vesicles, chylomicrons, lipoproteins, and the like. The polymers will normally be either addition or condensation polymers. Particulate CI derived therefrom will be adsorptive or functionalizable so as to bind, either directly or indirectly, an sbp member and a magnetic particle.

The particulate CI may be an analyte or may have an analyte that is bound thereto. The particulate CI may be formed from particles not initially bound to the analyte and derived from naturally occurring materials, naturally occurring materials which are synthetically modified and synthetic materials. The particles for use in assays will usually be polyfunctional and will have bound to or be capable of specific non-covalent binding to an sbp member, such as antibodies, avidin, biotin, lectins, protein A, and the like. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, J. Biol. Chem., 245 3059 (1970). The length of a linking group may vary widely, depending upon the nature of the compound being linked, the effect of the distance between the compound being linked and the particle on the binding of sbp members and the analyte and the like.

The particulate CI may have an electronic charge, either positive or negative. The particle can be inherently charged or can be treated chemically or physically to introduce a charge. For example, groups such as carboxyl, sulfonate, phosphate, amino, and the like can be chemically bound to or formed on the particles by techniques known in the art. Cells are normally negatively charged due to the presence of sialic acid residues on the cell surface. Latex particles can be positively or negatively charged but normally will have a negative charge as a result of the introduction of functional groups or absorption of charged polymers such as polypeptides, proteins, polyacrylate, and the like.

The particles can be fluorescent or non-fluorescent, usually non-fluorescent, but when fluorescent can be either fluorescent directly or by virtue of fluorescent compounds or fluorescers bound to the particle in conventional ways.

Label—A member of a signal producing system that may be bound to, or caused to bind to, a CI including analytes, or to a substance whose presence is related to the presence of the CI. The label can be isotopic or non-isotopic, usually non-isotopic, including catalysts such as an enzyme, a chromogen such as a fluorescer, dye or chemiluminescer, a particle, and so forth.

Signal Producing System—The signal producing system may have one or more components, at least one component being a label. The signal producing system generates a signal that relates to the presence or amount of CI, or a substance where presence is related to the presence of a CI, in a sample. The signal producing system includes all of the reagents required to produce a measurable signal. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of the degree of aggregation of particles or by use of electromagnetic radiation, desirably by visual examination.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Magnetic particles—particles that are intrinsically magnetically responsive or have been rendered magnetic by, for example, attachment to a magnetically responsive substance or by incorporation of such substance into the particles. The magnetic particles can be paramagnetic, ferromagnetic, or superparamagnetic, usually paramagnetic or superparamagnetic and will have magnetic susceptibilities ($\chi$) of at least $5 \times 10^{-5}$ emu/Oecm$^3$, usually at least $4 \times 10^{-4}$ emu/Oecm$^3$. The diameter of the magnetic particles should for the most part be relatively small, generally in the range from about 10 nm to 10 microns, preferably from about 40 to 1000 nm, more preferably from about 60 to 200 nm, most preferably colloidal.

Exemplary of the magnetic component of particles that are intrinsically magnetic or magnetically responsive are complex salts and oxides, borides, and sulfides of iron, cobalt, nickel and rare earth elements having high magnetic susceptibility, e.g. hematite, ferrite. The magnetic component of other such particles includes pure metals or alloys comprising one or more of these elements.

For the most part the magnetic particles will contain a core of the magnetic component with surface functional groups such as hydroxyl, silicate, carboxylate, sulfate, amino, phosphate and the like. Frequently, an additional surface coating will be employed that is covalently or non-covalently bound to the surface. The surface coating can be an anionic or cationic detergent, usually anionic; or the coating can be a protein such as albumin, immunoglobulin, avidin, fetuin or the like; or it can be a carbohydrate such as dextran, chitosan, amylose and the like, or combinations or these substances in their native form or functionalized so as to control their charge and hydrophilicity. Alternatively, the particles can be coated with other amphiphilic substances such as lipopolysaccharides, octyl glucoside, etc.

Alternatively, the magnetic component can be incorporated into a particle such as, for example, impregnating the substance in a polymeric matrix. However, this procedure frequently gives particles larger than the magnetic particles of this invention. For a more in-depth discussion of the preparation of magnetic particles by this method, see Whitesides, et al. (1983) *Trends in Biotechnology*, 1(5): 144–148 and references cited therein.

Preferred magnetic particles of less than a hundred nanometers in diameter can be made by precipitating iron oxides in the presence or absence of a coating such as a polysaccharide or protein. Magnetic particles of a few microns diameter can also be made by a ball milling process and removing material which is not in the size range of interest. Typically, magnetic particles formed by this latter process are quite polydisperse, and not as generally useful. More useful monodisperse metal oxide suspensions can be prepared by careful control of pH, temperature and concentrations during the precipitaion process. Coating the magnetic particles with macromolecules can increase their colloidal stability. This can be done by direct adsorption of high molecular weight polymers or by functionalizing the surface of the particle and then binding macromolecules to the functional groups. Emulsion polymerization and grafting techniques provide a means for coating magnetic particles with polymers.

In general, the magnetic particle that is best for a given task will be determined primarily by how the CI is to be bound to the magnetic particle or the size and properties of the particulate CI to be separated. For the isolation of cells and microorganisms, for example, the magnetic particles preferably should be readily suspendable, form stable, preferably colloidal, suspensions, and have high magnetic susceptibility. Where an sbp member is bound to the surface of the magnetic particle, its ability to bind to a complementary sbp member should be retained and should be stable with time.

Relatively small (<100 nm) magnetic particles are advantageously used the present separation procedures. These particles preferably have a homogenous core of metal, metal oxide or other metal compound. When colloidally stable, small particles can be suspended for long periods of time. Their large surface to volume ratio and relatively higher rates of diffusion enable them to quickly bind molecules and particles that are dispersed in the medium. Small magnetic particles are also less susceptible than large magnetic particles to aggregation due to residual magnetic moments after they have been exposed to a large applied magnetic field. Also, methods are known for colloidally stabilizing such small particles.

Magnetic particles of an intermediate size (100–1000 nm) can also be employed. They can be suspended readily and require a lower surface charge density to prevent spontaneous aggregation than do smaller particles. Magnetic particles of this size range can be created by emulsion polymerization and have the advantage of a surface that is easily modified whether by grafting or the covalent bonding of macromolecules to their surface. However, they remain suspended for shorter times and their lower surface to volume ratio decreases the rate of binding to the CI per unit volume of magnetic particles used.

Magnetic fluid—a colloidal suspension of magnetic particles in a liquid carrier that are not readily separated by a magnetic field. The resulting liquid has the bulk properties of a magnetic material. The fluid becomes spontaneously magnetized in the presence of an external magnetic field. The liquid also acts as a fluid and is capable of assuming the shape of its container, of flowing, and of moving around obstacles. Exemplary of a magnetic fluid is a ferrofluid where the suspended particles are ferromagnetic particles (see, for example, Rosenweig, supra, and U.S. Pat. No. 4,019,994, the disclosure of which is incorporated herein by reference, and Khalafolla, et al. (1980) *IEEE Transactions on Magnetics*, MAG-16: 178–183).

The colloidal magnetic particles can be coated with protein material, e.g., a serum protein such as albumin, gammaglobulin, etc., and the like. The colloidal magnetic particles can be mixed with an aqueous buffered solution of protein to prepare the protein-coated colloidal magnetic particles. The coating of the magnetic particles with protein can be accomplished by physical (e.g., absorption) or chemical binding.

Specific binding—the specific recognition of one of two different molecules for the other to the exclusion of other molecules. Generally, the molecules have an area on the surface or in a cavity giving rise to specific recognition between the two molecules. The primary binding influence arises from hydrogen bonding. Exemplary of specific binding are antibody-antigen interactions, enzyme-substrate interactions, and so forth.

Non-specific binding—non-covalent binding between, for example, particulate CI and magnetic particles, that is relatively independent of specific surface structures. Such non-specific binding will usually result from charge or electronic interactions between oppositely charged particles or between particles having the same charge where a polyionic reagent having a charge opposite thereto is employed. Non-specific binding may also result from hydrophobic interactions between particles.

Polyionic reagent—a compound, composition, or material, either inorganic or organic, naturally occurring or synthetic, having at least two of the same charge, either polyanionic or polycationic, preferably at least ten of the same charge; e.g., a polyelectrolyte.

Exemplary of polycationic reagents are polyalkylene amines such as polyethyleneimine and polypropyleneimine and their lower alkyl ammonium salts such as polybrene $(-N(CH_3)_2CH_2CH_2N(CH_3)_2CH_2CH_2CH_2CH_2-)_n$, metal ions such as calcium and barium ion, aminodextrans, protamine, positively charged liposomes, polylysine, and the like.

Exemplary of polyanionic reagents are heparin, dextran sulfate, negatively charged phospholipid vesicles, polycarboxylic acids, such as polyacrylate, polyglutamate and the like. The above materials and their preparation or isolation are well known in the art and many are commercially available.

Releasing agent—a compound, composition, or material, either naturally occurring or synthetic, organic or inorganic, capable of reversing the non-specific binding between, i.e., dissociating, particulate CI non-specifically bound to magnetic particles or reversing the specific binding between CI and magnetic particles. The releasing agent acts upon the non-specific bond between the particulate CI and the magnetic particles or the specific bond between CI and the magnetic particles. For example, where non-specific binding results from charge interactions, the releasing agent can act to change the pH of the medium to one which is unfavorable or incompatible with the charge interactions. The releasing agent can, therefore, be an acid such as a mineral acid or an organic acid or a base such as a mineral base or an organic base. Alternatively, the releasing agent can act to shield ionic interactions and thus can be a high ionic strength solution or a solution of a neutral polymer such as dextran. Alternatively, the releasing agent can have a charge which disrupts the non-specific binding between the particulate CI and the magnetic particles. Exemplary of the latter are be polyelectrolyte salts such as citrate, polyacrylate, dextran sulfate, and the like. Where the particles are bound by a polyionic bridge, the releasing agent can be a polyionic agent of opposite charge or can be a reagent which depolymerizes the polyionic reagent. Where the particulate CI and magnetic particles are of opposite charge, other positively or negatively charged polyelectrolytes or high ionic strength solutions may be used.

Where specific binding is involved the releasing agent can be one that disrupts the specific interactions such as, for example, chelating reagents such as ethylenediaminetetracetate (EDTA) which can disrupt metal-ligand bonding; reducing agents such as mercaptoethanol which can disrupt disulfide bonds; nucleophilic reagents such as hydroxylamine which can disrupt esters, excess ligand or receptor, or ligand or receptor mimic; where ligand-receptor binding is involved; and the like.

Ancillary Materials—Various ancillary materials will frequently be employed in a separation in accordance with the present invention. For example, buffers will often be present in the liquid medium, as well as stabilizers for the liquid medium and the other components. Frequently, in addition to these additives, additional proteins may be included, such as albumins, or surfactants, particularly non-ionic surfactants, binding enhancers, e.g., polyalkylene glycols, or the like.

As mentioned above, the present invention involves a method for separating a CI in a sample from other components in the sample. The method comprises contacting (1) a first liquid medium containing the CI bound to magnetic particles (CIMP), with (2) a second liquid medium that is of different density than and/or of different viscosity than the first liquid medium. The CI to be separated will be bound to the magnetic particle by specific or non-specific binding depending on the nature of the CI. Non-specific binding may be conveniently employed for particulate CI and is obtained as the result of charge interactions. For example, the particulate CI and the magnetic particles can have opposite electronic charges and non-specific binding will occur spontaneously. Where the particulate CI and the magnetic particles have the same charge, a polyionic reagent having an opposite charge can be added to the medium to cause non-specific binding between the particulate CI and the magnetic particles. Specific binding is generally employed for the binding of non-particulate CI to magnetic particles and may also be employed for binding of particulate CI to form CIMP. Usually, ligand-receptor binding is employed. The magnetic particles can have bound thereto an sbp member complementary to the CI.

The binding of CI to the magnetic particles is carried out in a first liquid medium. When the second liquid medium is miscible with the first liquid medium, the contacting of the media is carried out in such a way as to minimize or avoid mixing of the two media. This may be achieved by allowing one medium to flow onto the upper surface of the other medium which is stationary and of higher density or viscosity or both or which may be frozen or be a gel which is liquified by warming after contacting with the first medium. Alternatively, one medium can be introduced at the lower most portion of the other stationary medium by means of a delivery tube such as a pipette. Where the two liquid media are immiscible they need merely be combined and allowed to stand until they separate. After the above contacting of the first and second media takes place, the media are subjected to a magnetic field gradient to cause the CIMP to migrate into the second medium.

In carrying out the method, the first medium is a liquid, usually aqueous, medium. Other polar solvents may also be employed, usually oxygenated organic solvents from one to six, more usually from one to four, carbon atoms, including alcohols, ethers, and the like. Usually these cosolvents will be present in less than about 40 weight percent, more usually in less than about 20 weight percent. The pH for the medium will usually be selected to promote specific or non-specific binding of the CI to the magnetic particles prior to separation. Where the particles are negatively charged, increasing the pH will tend to increase the charge and prevent spontaneous aggregation caused by non-specific hydrophobic and van der Waals interactions. The converse applies to positively charge particles. Where an oppositely charged polyelectrolyte is added to cause binding, changes in pH that increase the charge of the polyelectrolyte will often decrease the charge of the particles and an optimum pH must be selected that will avoid the use of excessive amounts of this reagent. Generally, a pH range of 5 to 10, more usually 6 to 9, will be used. For ligand-receptor binding other considerations with respect to pH are to maintain a significant level of binding of sbp members, for example, or nucleic acids. Various buffers may be used to achieve the desired pH and maintain the pH during the determination. Illustrative buffers include borate, phosphate, carbonate, Tris, barbital, and the like. The particular buffer employed is not critical to this invention; however, in individual separations, one buffer may be preferred over another. When particulate CI is involved, a reagent that promotes reversal of the binding of the particulate CI and the magnetic particles can be added after the separation has been accomplished.

The second liquid medium may be aqueous or non-aqueous. When aqueous, the second liquid medium will usually differ in viscosity and/or density from the first medium and may be miscible or immiscible. When non-aqueous it will be immiscible in the first medium and may be organic or inorganic such as halocarbons, hydrocarbons, silicon fluid, ethers, esters, and the like.

Moderate temperatures are normally employed for carrying out the method and usually constant temperatures during the period for conducting the method. Generally, the temperatures will be chosen to promote specific or non-specific binding of the CI to the magnetic particles prior to separation. The temperature for the method, will generally range from about 0° to 50° C., more usually from about 15° to 40° C. Again, after the separation is accomplished a temperature that promotes reversal of the binding of the CI and the magnetic particles can then be chosen.

The concentration of the magnetic particles in the medium will depend on the amount of CI in the medium that is to be separated and whether it is particulate or non-particulate, the rate of separation that is desired, the magnetic field gradient and field strength, the magnetic susceptability of the magnetic particles the relative density and/or viscosity of the first and second media, and the like. In general, higher concentrations of magnetic particles provide more efficient and rapid separations but too high a concentration can cause excessive entrainment of the medium. The concentration is normally determined empirically and will generally vary from about 0.1 to 1000 $\mu$g/ml, more usually from about 0.5 to 200 $\mu$g/ml, frequently from about 1 to 50 $\mu$g/ml.

Where particulate CI is to be separated from a medium, the concentration of the particulate CI can vary widely depending upon the need. For example, in separation of cells from blood, the cell volume may represent 50% of the total volume of the blood. By contrast, it may be desired to separate as few as 1000 bacteria/ml from a sample of water. Where the CI is non-particulate and becomes bound to a magnetic particle, the CI will generally vary from about $10^{-4}$ to $10^{-14}$M, more usually from about $10^{-6}$ to $10^{-12}$M. Where non-magnetic particles are added to the medium and bind to a specific binding pair member in the medium to provide particulate CI, their concentration will depend on numerous factors such as particle size and surface area, and concentration of the sbp member. In general, added non-magnetic particle concentrations will be about 0.01 to 100 $\mu$g/ml, more usually from about 0.1 to 20 $\mu$g/ml. Considerations such as the concentration of the sbp member, specific and non-specific binding effects, desired rate of the reaction, temperature, solubility, density and/or viscosity, and the like will normally determine the concentration of other reagents.

While the concentrations of the various reagents will generally be determined by the concentration range of interest of the CI to be separated, the final concentration of each of the reagents will normally be determined empirically to optimize the rate and extent of separation of the CI.

Chemical means for forming non-specific bonds between particulate CI and magnetic particles will usually be added to the first liquid medium. Except where particulate CI are to be separated that have an opposite charge to the magnetic particles, this chemical means is usually a polyionic reagent having a charge opposite to that of the particles. The amount of polyionic reagent added should be sufficient so that substantially all of the particulate CI becomes bound to the magnetic particles. This concentration should be determined empirically. Excess reagent should generally be avoided where it interferes with complete binding between particulate CI and the magnetic particles. Generally, the polyionic reagent will have a concentration in the liquid medium sufficient to provide a number of ions associated with the polymer and equal to the total number of charges of opposite sign on all the particles in the medium. Where particulate CI are to be separated that have an opposite charge to the magnetic particles, the chemical means for forming non-specific bonds between the particles will frequently be a low ionic strength buffer.

The binding of CI to magnetic particles can be affected by pH. The binding can also be affected by other factors such as ionic strength and the presence of ionic and non-ionic polymers. Generally, where non-specific binding is due to charge interactions, the ionic strength should be chosen initially to facilitate the binding between the particles. For this purpose the ionic strength is generally low and can be in the range of less than 0.0001 to 0.5M, preferably 0.001 to 0.1M. Where the particles are negatively charged, the pH will usually be high and can be in the range of 4 to 12, preferably 8 to 10. After the separation has been completed, the ionic strength can be adjusted upward or the pH downward to facilitate the reversal of the coupling of the particulate CI and the magnetic particles. For this purpose, the ionic strength of the medium will normally be from about 0.1 to 3M or higher, preferably from about 0.15 to 1M and the pH will be 1 to 8, preferably 3 to 6. The principles for causing particles to aggregate or to remain suspended are well known in the field of colloid science. Where specific binding is involved, conditions that inhibit non-specific binding will usually be used as described above for reversal of non-specific coupling.

After the magnetic particles have been added to the liquid medium and where specific binding of CI to the magnetic particles is utilized, the liquid medium is then held for a period of time sufficient for this binding to occur. Normally this requires 0.5–120 minutes, more frequently 1–60 min. Where chemically induced non-specific binding of particulate CI to magnetic particles is involved, such binding will usually occur essentially instantaneously, and it is usually sufficient to allow the mixture to stand for 60 sec., frequently less than 15 sec.; preferably the magnetic field is applied immediately after contacting of the first and second media. The extent of binding between the CI or the particulate CI and the magnetic particles controls the efficiency of the magnetic separation.

Next, the first liquid medium is contacted with a second liquid medium that has a different density and/or viscosity than the first medium. Generally, where the densities are different, the density of one medium is at least 1.05 times the density of the other medium, usually about 1.1 to 1.4 times the density of the other medium. The second medium is an aqueous or non aqueous medium and may include polar solvents as described above for the first medium.

The relatively higher density of one of the media can be achieved by selecting a solvent that has an intrinsically high density relative to water such as a halocarbon solvent or an intrinsically low density such as a hydrocarbon solvent wherein the solvents are immiscible with the first aqueous medium. Alternatively when both media are aqueous, a high density solute can be added to one of the media to achieve the desired density prior to contact of the two media. Preferably, the high density solute will not readily cross cell membranes (where cells are to be separated) nor add substantially to the ionic strength of the medium. Exemplary of such high density solutes are non-ionic, water soluble polyiodinated solutes, which are commercially available under the tradenames HYPAQUE and Nycodenz. Other high density solutes include high molecular weight salts such as cesium chloride, and the like, sucrose, etc. The use of high molecular weight salts can be less desirable where viable microorganisms are to be separated.

In any of the above preparations, the medium may be sufficiently agitated, after addition of the appropriate agent and prior to contact with the first medium, to ensure uniform distribution of the agent in the medium, thus achieving uniform density and/or viscosity in the medium where needed.

Where one medium is chosen to be more viscous than the other medium, the viscosity of the one medium is at least 1.5 times the viscosity of the other medium, usually about 2 to 100 times the viscosity, preferably about 2.5 to 75 times the viscosity, of the other medium. Generally, the viscosity of one medium is in the range of 0.6 to 1.3 cp and that of the other medium is 1.5 to 100 cp or higher.

A higher viscosity of one medium can be achieved by including as part of the medium a solute that will increase bulk viscosity, for example, a polyol such as glycerol or polyvinylalcohol, a saccharide, such as mono and polysaccharides including, by way of example and not limitation, mannitol, glucose, agar, agarose, sucrose, starch, dextran, or hydrophilic polymers such as polyethyleneglycol, polyacrylate, polyvinylpyrollidone; and the like. The viscosity of the medium can be controlled not only by the concentration and nature of the solute, but also by temperature where it is desirous to achieve such control. The viscosity of the medium can be controlled by adjusting temperature where an increase in temperature will usually cause the medium to have a lower viscosity.

After contacting of the first and second media, a magnetic field is applied to cause the CIMP to migrate from the first medium into the second medium. The application of a magnetic field to the medium can be carried out in any conventional manner that provides for a high magnetic field gradient. The media will normally be in a container made of non-magnetic material, for example, glass or plastic. In applying the magnetic field, the reaction container can be placed in close proximity to an electromagnet or permanent magnet, preferably permanent, which has a geometry to maximize the field intensity and gradient within the media. The higher the strength of the magnetic field and the higher the gradient, the faster the migration. Normally, it will be convenient to carry out the separation in a tube of diameter from about 2 to 50 mm, preferably from about 3 to 15 mm, with one or more permanent magnets mounted as close to the tube as practical to provide field strengths of at least about 200 Oe and preferably at least about 1KOe with magnetic field gradients usually at least about 20 KOe/cm. The magnetic field is applied for a sufficient period of time to provide the desired degree of migration of the CIMP into the second medium. Depending on the geometry, field strength, magnetic susceptibility of the particle and the like, the magnetic field is applied for a period of about 2 seconds to 1 hour, preferably about 5 seconds to 60 seconds.

Once the CIMP has migrated from the first medium into the second medium the media can be separated from one another by any convenient means such as, for example, decantation, pipeting, and the like.

Where desired, the CIMP can be separated from the second medium by any convenient method such as, for example, filtration, decantation or pipetting. The separated CIMP can be treated to reverse the binding between the CI and magnetic particles. The reversal of the binding between the CI, whether particulate or non-particulate, and the magnetic particles is dependent upon the nature of the binding between the particles. For example, the CIMP can be suspended in a liquid medium with reagents added to facilitate reversal of the binding. In one approach, where particulate CI is bound to magnetic particles by ionic interactions, ionic strength and the pH of the medium can be adjusted to facilitate reversal of the binding. Generally, increasing the ionic strength will reverse electrostatic binding. Where the particulate CI and magnetic particles are oppositely charged, a change in pH that reverses the charge on one of the particles will reduce binding interactions. Alternatively, when both particles are negatively charged a polycationic binding agent can be used to cause binding and decreasing the pH sufficiently to neutralize the charge on the particles can reverse binding. Thus, it may be desirable to change the pH to as high or low value as allowed by the stability of the reagents, usually no less than pH 3 or greater than pH 10.

Where non-specific binding results from charge interaction, an agent other than an acid or base can be added to reverse the charge interactions responsible for the non-specific binding. For example, a releasing agent can be added. Where the particles have like charges and an oppositely charged polyelectrolyte was the chemical means for binding the particles, a polyelectrolyte of the same charge as on the particles can be used to dissociate the particles. The polyelectrolytes can be, for example, polyanions such as dextran sulfate, heparin, polyglutamate, polyacrylate, phospholipid vesicles, carboxymethyldextran and citrate. Aminodextran, chitosan, polybrene, polyethyleneimine, and cationic liposomes are exemplary of polycations that can be employed.

Where a polycation was used to initiate non-specific binding between the particulate CI and the magnetic particles, a polyanion can be employed to reverse the binding. Alternatively, where a polyanion was used to form the non-specific binding between the particles and the magnetic particles or between the magnetic particles, a polycation can be used to reverse the binding. For example, where polycations such as polybrene or barium ion have been employed, the releasing agent can be a polyanion such as citrate or sulfate. Detergents can act as a releasing agent for liposomes and when particles are non-specifically aggregated primarily through hydrophobic interactions.

For particulate or non particulates CI that is specifically bound to the magnetic particles through ligand-receptor binding the free ligand or receptor can act as the releasing agent. Where binding is covalent, a hydrolytic or redox reagent that can disrupt the covalent binding will usually be used.

The concentration of the releasing agent should be sufficient to result in substantial or complete reversal of the binding between particulate CI and the magnetic particles. The concentration of the releasing agent is generally dependent upon the nature of binding between the particulate CI and the magnetic particles and the nature of the CI. Generally, for particulate CI the concentration of the releasing agent will be at least equal to the concentration of ionic or hydrophobic sites on the particulate CI, preferably at least 10 fold higher.

It is important to choose the releasing agent with regard to the nature of the CI so as to minimize or avoid damage to the CI after the release from the CIMP, especially where particulate CI such as cells or microorganisms are involved.

Once the CI has been released from the CIMP, it may be used as desired. For example, the released CI can be examined for the presence of a detectable signal in relation to the amount of an analyte in the sample. Generally, a label is employed, either initially or in a subsequent detection step. Released particulate CI can be cells which can be used as desired. For example, the released particulate CI can be red blood cells or microorganisms. If detection of cells or microorganisms is desired, one may utilize an agent that will incorporate into the membrane of the material to be detected. For example, intercalation dyes such as squarates or cyanines can be employed.

In one embodiment of the invention, the magnetic particles are provided as a magnetic liquid, e.g., ferrofluid. The CI to be separated is combined with the magnetic liquid.

One application of the present method is the removal of cells from a sample containing cells such as, for example, removal of red blood cells from whole blood. In the method, using whole blood by way of example and not by way of limitation, a whole blood sample is combined in a first liquid medium with charged magnetic particles under conditions for non-specific binding of the magnetic particles to the cells. The cells will usually have a negative charge by virtue of sialic acid residues or the like on the surface of the cells. The magnetic particles can be positively charged, resulting in direct non-specific binding between the cells and the magnetic particles. Preferably, the magnetic particles have a negative charge. In this latter instance a polycationic reagent is included in the liquid medium to provide conditions for non-specific binding between the cells and the magnetic particles. Useful polycationic reagents in this method can be, for example, polybrene, polyalkyleneimines, aminodextran, chitosan, and positively charged liposomes. The preferred polycationic reagent for removing cells from whole blood is polybrene or polyethyleneimine.

Next, the first liquid medium can be contacted with, without mixing with, a second liquid medium of different density and/or viscosity than the first medium. The media can be subjected to a magnetic field gradient to cause the cell-magnetic particle complex to migrate from the first liquid medium into the second liquid medium. Application of the magnetic field results in concentration of the cell-magnetic particle complex in the second medium, which permits its separation from the cell-free first medium by, for example, decantation, pipetting, etc.

The separated cell-magnetic particle complex can then be treated to release the cells from the complex as described above. Where polybrene or polyethyleneimine is employed as a polycationic binding agent, preferred releasing agents are citrate or polyacrylate.

The present method provides particular advantages for automated blood typing procedures by providing a way to prepare blood plasma without centrifugation. It is also useful in the Coombs antiglobulin test where immunoglobulin-containing plasma is first combined with test cells and must then be fully removed in order to determine if antibodies from the plasma have bound to the cells.

The present invention has application to assays for an analyte in a sample suspected of containing the analyte. The analyte is an spb member. The analyte may be a non-particulate CI or can form a particulate CI by binding to a particle by means of a complementary sbp member that is or becomes bound to the particle. Either the analyte, or a substance whose presence is related to the presence of the analyte, such as, e.g., an antigen removed from the surface of a cell, an sbp member reciprocal (complementary) to the analyte or the like, can be the CI. In the assay the CI may be combined in an aqueous medium with magnetic particles having an sbp member complementary to the CI. Alternatively, a bridging sbp member can be employed to bind to both the CI and a magnetic particle having an sbp member on its surface. For particulate CI, a polyionic reagent can be added to bind the particulate CI to the magnetic particles. In the present invention magnetic particles are added to the medium under conditions for binding of the magnetic particles to the CI or particulate CI.

The aqueous medium is contacted with a second medium which is of different density and/or viscosity than the aqueous medium. The media are then subjected to a magnetic field gradient to cause the CI complexed with the magnetic particles (CIMP) to migrate from the aqueous medium into the second medium. The assay will normally involve a signal producing system for producing a detectable signal in relation to the amount of analyte in the sample. The signal producing system usually includes a labeled sbp member. The CIMP in the second medium may be further combined with none, one or more members of the signal producing system. The second medium can then be examined for the presence of a detectable signal. Such a determination can require the addition of any remaining members of the signal producing system not added above. Alternatively, the CIMP can be separated from the second medium and treated and examined for a detectable signal utilizing remaining members of the signal producing system. Alternatively, the CIMP can be treated to separate CI from the magnetic particles prior to examining for the presence of a detectable signal. After the CI has been separated from the magnetic particles, the CI may be examined for the presence of a detectable signal produced in relation to the amount of analyte in the sample. For this purpose they can be combined with any remaining members of the signal producing system not added above in order to generate a detectable signal.

The invention further comprises a composition comprising (1) a first liquid medium containing magnetic particles to which are bound a component of interest (CI) and in contact but substantially unmixed therewith (2) a second liquid medium having a different density and/or viscosity or immiscibility with the first liquid medium. The composition may further comprise a polyionic reagent of opposite charge to the magnetic particles. Alternatively, in the composition of the invention the magnetic particles can have a CI bound to an sbp member bound thereto.

As a matter of convenience, the reagents for conducting a separation in accordance with the present invention can be provided in a kit in packaged combination in predetermined amounts for use in such separation. The components of the kit can be packaged separate or one or more components of the kit can be packaged together depending on the interreactivity of such components. The kit can comprise magnetic particles, means for providing a high density or high viscosity aqueous medium or a water immiscible liquid medium. The kit can further include means for causing the magnetic particles to bind to a component of interest or to a particle having a component of interest bound thereto. For example, the magnetic particles can have an sbp member, bound to the surface. The sbp member is complementary to a CI and provides means for binding CI to the magnetic particles. The kit can include a polyionic reagent for binding a particulate CI to the magnetic particles. Additionally, a releasing agent can be included for releasing particulate CI from the magnetic particles. The kit may also include non-magnetic particles with an sbp member bound thereto. Such sbp member can be complementary to an analyte.

For assays the kit can comprise an sbp member complementary to the analyte, or an sbp member bound to a charged particle if neither the analyte nor the complementary sbp member is bound to a charged particle and charged magnetic particles or magnetic particles having an sbp member bound thereto. The kit can also include reagents for generating a signal in relation to the amount of analyte in the sample. Furthermore, the kit can comprise a polyionic reagent having a charge opposite to that of the particles when all the particles have the same charge. Additionally, the kit can further comprise a releasing agent for reversing the binding between the particles. Ancillary agents can be included as necessary.

EXAMPLES

The invention is described further by the following illustrative examples. All parts and percentages herein are by volume unless otherwise indicated. Temperatures are in degrees Centigrade (°C.).

Example 1

Separation of Red Blood Cells

A. Preparation of Colloidal Magnetic Iron Oxide (Ferrofluid)

A solution of 20 ml 2M $FeCl_3$, 10 ml 2M $FeCl_2$, and 20 ml 1M HCl was added dropwise over five minutes with stirring to a solution of 25 ml concentrated $NH_4OH$ in 500 ml water. The precipitate settled out, and the supernatant was decanted. The residue was stirred for two minutes with 500 ml 2M $HClO_4$ and again allowed to settle out. The supernatant was decanted, and the residue was taken up in water and dialyzed against 10 mM $HClO_4$. The resulting colloid had a volume of 80 ml and an iron content of 28 mg/ml. The average particle size as determined by dynamic light scatter was 60 nm. Literature reference-R. Massart, *C. R. Acad. Sci. Paris*, 291C, 1 (1980).

B. Coating of Colloidal Magnetic Iron Oxide with Succinylated Bovine Serum Albumin (sBSA)

A solution of 105 ml of 9.5 mg/ml sBSA (prepared by treatment of 5.0 g BSA in 250 ml 0.1M sodium phosphate, pH 8.0 with 0.20 g succinic anhydride) in water was adjusted to pH 3.38 with 0.1M $HClO_4$. A solution of 30 ml of 35 mg/ml colloidal magnetic iron oxide in 10 mM $HClO_4$ was diluted with 75 ml water and added to the sBSA solution. The pH of the solution was then adjusted to pH 9.06 with 1M $NMe_4OH$. The average particle size in the resulting colloid was determined by dynamic light scatter to be 63 nm.

C. Separation

The sample used in this example was prepared by combining:

10 µl of a 10% red blood cell suspension in phosphate buffered saline containing 16 g/ml glycine, 0.03M NaCl, 0.015M phosphate, pH6.7 (PBS), 50 µl of plasma, 50 µl of low ionic strength solution containing 0.003M phospate, 0.24M glycine, and 0.03M NaCl, pH6.7 (LISS)

The sample was placed in a 12 mm×75 mm glass test tube. An aqueous suspension (15 µL) of colloidal magnetic iron oxide particles BSA (prepared as in A and B above) and LISS (300 µl) were added to the test tube and mixed by vortexing. Polybrene (20 µl of 16 mg/ml, in LISS from Aldrich Chemical Co.) was added to the test tube and mixed by vortexing. The resulting solution was carefully underlaid with 500 µl of 7.5% sucrose dissolved in LISS. Two magnets (2 Kgauss each) were used for the separation. These were placed with opposing poles at about 900 to each other near the bottom of the tube and below the sample-sucrose interface. Complete migration of the cell-magnetic particle aggregates to the sides of the tubes near the magnets was observed visually to occur in 1–2 minutes. The liquid media were aspirated and the aggregates, held tightly to the tube by the magnets, were gently rinsed with 1.0 ml of LISS. The coaggregation of cells and magnetic particles was completely reversed by gentle agitation of the glass tube after the addition of 20 µl of polyacrylate (5 mg/ml) from Aldrich Chemical Co. Reversal was apparent by the observed complete resuspension of the cells and the detection of only non-aggregated cells using a fiber optic spectrometer as described in U.S. Pat. No. 4,564,598.

Example 2

Capture and Separation of Bacteria

Affinity-purified goat anti-rabbit antibody (Kirkegaard and Perry Laboratories, Gaithersburg, Md.), human serum absorbed) was covalently bound to a 0.8 micron diameter styrene/vinylcarboxylic acid latex containing 42% magnetite (Bangs Laboratories).

*Escherichia coli*, strain K-12, ATCC 10798 were grown on Tryptic Soy Agar (TSA) plates overnight at 37° C. in a 5% $Co_2$ incubator. Bacteria were suspended in 1 mL PBS, pH 7.5, and washed by centrifugation in a Microfuge for 2 minutes at room temperature. The bacterial pellet was resuspended at 1E9 CFU/mL in PBS, pH 7.5, containing 1% BSA and 50 µg/mL polyclonal rabbit anti-*E. coli* (DAKO), and the cells were incubated for 30 minutes at room temperature.

The bacteria were centrifuged as described above and washed 3 times using PBS, 1% BSA, pH 7.5, to remove excess unbound rabbit antibody. A second aliquot was similarly processed with antibody omitted as a control. Both suspensions were diluted to approximately 2E4/mL in PBS/BSA before use.

Whole blood preserved with CPD (citrate/phosphate/dextrose) was lysed in a DuPont Isolator tube for 5 minutes as specified by the manufacturer.

Anti-rabbit magnetite latex (75 µL) (prepared above) was added to each of four 12×75 mm polypropylene test tubes followed by 1 mL of PBS/BSA. The latex was removed magnetically on a Corning magnetic separator, allowing about 10 minutes for separation, then resuspended in 70 µL PBS/BSA. Lysed blood (125 µL), PBS/BSA (45 µL), and coated or uncoated bacteria (10 µL) were added, and the tubes were placed on a rotary shaker for 40 minutes at room temperature at medium speed.

Four shells vials (15×45 mm) were rinsed with sterile PBS/BSA, and 1 mL of 55.5% w/v Nycodenz® (Accurate Scientific, New York, N.Y.), 1 mg/mL polyvinyl pyrrolidone (PVP) was added to each. The bacterial reaction mixtures were carefully layered over the Nycodenz. The reaction tubes were rinsed with 250 µL PBS/BSA, which was added to the vials. A disk-shaped magnet was placed under each tube, using cobalt-samarium magnets for one pair of positive and negative tubes and neodymium magnets for the other. Formation of a brown film on the bottom of each tube was observed within a few minutes. This process appeared to be complete within 10–20 minutes even with the weaker cobalt-samarium magnets. No trace of any red color or turbidity was noted either in the Nycodenz or on the particles.

After 30 minutes the supernatant was carefully removed from each tube and spread on a TSA plate. The film of magnetic particles was resuspended in 1 mL PBS with gentle mixing and similarly spread on a plate. Finally, each tube was washed with 1 mL of PBS with vortex mixing and the wash was spread. The plates were allowed to stand undisturbed until all of the liquid was absorbed into the agar (several hours at room temperature), then further incubated overnight at 37° C.

Results were read by counting colonies and are tabulated below as colony forming units (CFU)/fraction.

| Antibody:    | +   | +   | −   | −   |
| --- | --- | --- | --- | --- |
| Supernatant: | 2   | 0   | 440 | 447 |
| Pellet:      | 223 | 215 | 9   | 10  |
| Wash:        | 33  | 4   | 1   | 0   |

Nominal total inputs as measured on separate plates were 168 and 146 bacteria for duplicate positive and 478 and 455 for duplicate negatives.

The invention described herein provides for a simple, effective, and complete separation of a component of interest from other components in a sample. A significant advantage of the present invention is that washing of the compound of interest free of other components occurs during passage into and within the higher density and/or higher viscosity medium.

Although the foregoing invention has been described in some detail by way of illustration and example for the purposes of clarity and understanding, it will be obvious that certain changes or modifications may be practiced within the scope of the appended claims.

What is claimed is:

1. A method for the separation of a particulate biologic material (PBM) from a mixture containing said PBM and other components, which method comprises:

combining in a first liquid medium said PBM and said other components, and magnetic particles having immobilized thereon a member of a specific binding pair (sbp) that specifically binds to said PBM to form a complex of said PBM and said magnetic particles (PBMMP), layering said first liquid medium with a second liquid medium that is of different density and/or viscosity than said first liquid medium such that said first medium is layered above said second medium, subjecting said first liquid medium and said second liquid medium to a magnetic field gradient whereby said PBMMP migrates into said second liquid medium and is washed thereby, and separating said PBMMP from said second medium.

2. The method of claim 1 wherein said second liquid medium is a solution of a polysaccharide.

3. The method of claim 2 wherein said polysaccharide is sucrose.

4. The method of claim 1 wherein the density of said second liquid medium is at least 1.1 times that of said first liquid medium.

5. The method of claim 1 wherein the viscosity of said second liquid medium is at least twice that of said first liquid medium.

6. The method of claim 1 wherein said magnetic particles are paramagnetic or superparamagnetic.

7. The method of claim 6 wherein said particles are 10–100 nm average diameter.

8. The method of claim 1 wherein said PBM is an erythrocyte.

9. The method of claim 1 wherein said PBM is a ligand or a receptor bound to said magnetic particles by means of ligand-receptor binding.

10. The method of claim 1 which further comprises the step of treating said separated PBMMP with a releasing agent to reverse their specific binding.

11. A method for separating cells from a mixture containing said cells and other components, which method comprises:

combining in an aqueous medium said cells and said other components, and superparamagnetic or paramagnetic particles having immobilized thereon a member of a specific binding pair (sbp) that specifically binds to said cells to form a complex of said cells and said superparamagnetic or paramagnetic particles (cell-particles), layering said aqueous medium with a second liquid medium that is of different density and/or viscosity than said aqueous medium such that said aqueous medium is layered above said second medium, subjecting said aqueous medium and said second liquid medium to a magnetic field gradient sufficient to cause said cell-particles to migrate into said second medium and to be washed thereby, and separating said cell-particles from said second medium.

12. An assay method for the determination of a particulate biological material (PBM) that is an analyte, in a sample suspected of containing said PBM and other components, said method comprising;

(a) combining in a first liquid medium,
   said sample,
   magnetic particles having immobilized thereon a member of a specific binding pair (sbp) that specifically binds to said PBM to form a complex of said PBM and said magnetic particles (PBMMP),
a labeled sbp member that specifically binds to said PBM, such that said labeled sbp member can be separated from said first liquid medium in relation to the concentration of said PBM in said sample;

(b) layering said first liquid medium with a second liquid medium that is of different density and/or viscosity than said first medium, such that said first medium is layered above said second medium;

(c) subjecting said first liquid medium to a magnetic field gradient whereby said PBMMP migrates into said second liquid medium and is washed thereby;

(d) separating said PBMMP from said second liquid medium;

(e) examining said second medium, said separated PBMMP or said PBM for the presence or amount of said labeled sbp member, the presence or amount thereof indicating the presence or amount of said PBM in said sample.

13. The method of claim 12 wherein said labeled sbp member includes a label selected from the group consisting of enzymes and chromogens.

14. The method of claim 12 wherein said second liquid medium is a solution of a polysaccharide.

15. The method of claim 12 wherein the density of said second liquid medium is at least 1.1 times that of said first liquid medium.

16. The method of claim 12 wherein the viscosity of said second liquid medium is at least twice that of said first liquid medium.

17. The method of claim 12 wherein said magnetic particles are 10–100 nm average diameter.

18. The method of claim 12 wherein said PBM is specifically bound to said magnetic particles by means of ligand-receptor binding.

19. The method of claim 12 which further comprises the step of treating said separated PBMMP with a releasing agent to reverse their specific binding.

* * * * *